United States Patent [19]
Breitkopf

[11] Patent Number: 5,034,008
[45] Date of Patent: Jul. 23, 1991

[54] ELASTICIZED ABSORBENT ARTICLE

[75] Inventor: Stephen Breitkopf, North Brunswick, N.J.

[73] Assignee: Chicopee, New Brunswick, N.J.

[21] Appl. No.: 432,945

[22] Filed: Nov. 7, 1989

[51] Int. Cl.$^5$ .............................................. A61F 13/15
[52] U.S. Cl. .............................................. 604/385.2
[58] Field of Search .............................. 604/385.2, 369

[56] References Cited

U.S. PATENT DOCUMENTS

| | | | |
|---|---|---|---|
| 3,081,515 | 3/1963 | Griswold et al. | 604/376 |
| 4,205,679 | 6/1980 | Repke et al. | 604/385.2 |
| 4,324,245 | 4/1982 | Mesek et al. | 604/370 |
| 4,325,372 | 4/1982 | Teed | 604/385.2 |
| 4,333,782 | 6/1982 | Pieniak | 604/373 |
| 4,341,213 | 7/1982 | Cohen . | |
| 4,417,935 | 11/1983 | Spencer | 604/385.2 |
| 4,425,127 | 1/1984 | Suzuki et al. | 604/369 |
| 4,450,026 | 5/1984 | Pieniak et al. | 604/385.2 |
| 4,527,989 | 7/1985 | Karami | 604/385.2 |
| 4,639,949 | 2/1987 | Ales et al. | 604/385.2 |
| 4,642,819 | 2/1987 | Ales et al. | 604/385.2 |
| 4,675,016 | 6/1987 | Meuli et al. | 604/385.2 |
| 4,685,916 | 8/1987 | Enloe | 604/385.2 |
| 4,687,477 | 8/1987 | Suzuki et al. | 604/385.2 |
| 4,718,901 | 1/1988 | Singheimer | 604/385.2 |
| 4,726,807 | 2/1988 | Young et al. | 604/385.2 |
| 4,753,834 | 6/1988 | Braun et al. | 428/74 |

Primary Examiner—John D. Yasko
Assistant Examiner—Sharon Rose
Attorney, Agent, or Firm—Mavis K. Fowler

[57] ABSTRACT

An elasticized absorbent article, illustrated as an elastic waistband disposable diaper, includes an absorbent panel, a backsheet underlying the absorbent panel, and a liquid-permeable topsheet which overlies the absorbent panel. Each of the backsheet and topsheet includes at least one longitudinal end marginal portion which extends beyond an end edge of the absorbent panel. A waist elastic element is provided which is positioned between the end marginal portions of the topsheet and backsheet for forming an elastic waistband region. Notably, the elastic waistband element is provided with a substantially overall adhesive coating, preferably in either slot-coated or spray-coated filament form, for securement to the associated topsheet. The topsheet is thereby elastically gathered to provide a textured and cushioned surface at the inside region of the waistband for enhanced comfort. The preferred provision of another substantially overall adhesive coating for securing the waist elastic element to the backsheet desirably enhances the containment characteristics of the diaper.

29 Claims, 2 Drawing Sheets

ELASTICIZED ABSORBENT ARTICLE

TECHNICAL FIELD

The present invention relates generally to absorbent articles such as disposable diapers and the like, and more particularly to a construction for elasticizing an absorbent article, such as the waistband of a disposable diaper or incontinence device, which provides enhanced comfort for the wearer.

BACKGROUND OF THE INVENTION

In recent years, disposable absorbent articles such as disposable diapers have become increasingly popular by virtue of both their convenience and containment characteristics. In a typical disposable diaper construction, an absorbent medium, ordinarily comprising wood pulp fiber and superabsorbent polymers, is positioned between a liquid-permeable facing layer, and a backing layer, at least a portion of which is liquid impermeable. Adhesive tape tabs are ordinarily provided for securing the diaper in position on the wearer, with elastication at the leg openings provided for enhanced containment and fit.

In addition to these typical components, one or both waist portions of the diaper, corresponding to the front and rear portions of the diaper, may be elasticized. In such a construction, an elastic element is provided at the waist portion, typically between the associated facing and backing layers. When the diaper is fitted to the wearer, the elasticized waist portion cooperates with the adhesive tape tabs of the diaper so that the diaper yieldably conforms to the waist of the wearer.

U.S. Pat. No. 4,515,595, to Kievit et al., discloses one such elastic waist construction for a diaper. In accordance with the teachings of this patent, an elastic element is provided between the backing and facing layers at the waist portion of the diaper, with the elastic element secured to each of these layers by spaced regions of securement, between which are provided regions of non-securement. This results in the formation of relatively coarse corrugations in each of the backing and facing layers adjacent to the waist elastic member.

This patent states that the formation of such corrugations allows the diaper to breath by permitting the exchange of air and vapor between the interior of the diaper and the surrounding atmosphere. It is believed that the regions of non-securement can function in the nature of liquid channels and undesirably impair the liquid containment characteristics of the diaper, thereby undesirably contributing to leakage of the diaper. Moreover, the relatively coarse corrugations which are formed in accordance with the teachings of this patent are not particularly aesthetically pleasing, nor do they present a Particularly smooth and comfort-enhancing surface to the wearer.

The present invention concerns an elasticized disposable absorbent article which is illustrated as a disposable diaper having an elasticized waistband construction particularly configured for enhanced comfort and containment characteristics.

SUMMARY OF THE INVENTION

In accordance with the present invention, an elasticized absorbent article is disclosed wherein an elastic element of the construction is provided with a substantially overall coating of adhesive, in either a continuous layer or in a filament-type form, for securement of the element to the associated topsheet of the article. By this construction, a large plurality of relatively small surface irregularities are formed at the inside surface of the topsheet, thus providing a desirably textured and cushioned surface for contact with the wearer for enhanced comfort.

In the preferred form, a substantially overall coating of adhesive is also provided between the elastic element and the associated backsheet of the article. Again, the adhesive may be in either a continuous layer or a filament-type form distributed substantiallY throughout the respective expansive surface of the elastic element. This preferred arrangement avoids the formation of any channels or like liquid-conducting passages spanning the elastic element. Thus, leakage past the elastic element is substantially eliminated, thereby enhancing the containment characteristics of the article.

In accordance with the illustrated embodiment of the present invention, an elasticized absorbent article embodYing the invention is disclosed as an elastic waistband disposable diaper. The diaper includes an absorbent panel, which may typically comprise comminuted wood pulp fiber, with or without the addition of supplementary hydrocolloid superabsorbent material.

The diaper further includes a backsheet positioned beneath the absorbent panel, with at least a portion of the backsheet being liquid impermeable. In accordance with the illustrated embodiment, the backsheet includes at least one longitudinal end marginal portion which extends beyond the absorbent panel, as well as opposite side margins extending laterally beyond opposite side edges of the panel.

The disposable diaper further includes a liquid-permeable topsheet overlying the absorbent element, with the topsheet material comprising nonwoven fabric. Like the backsheet in the illustrated embodiment, the topsheet includes at least one end marginal portion which extends beyond the absorbent panel, which end marginal portion is longitudinally coextensive with the end marginal portion of the backsheet. Additionally, the illustrated diaper is configured such that the topsheet includes opposite side marginal portions which extend laterally beyond opposite side edges of the absorbent panels.

In accordance with the present invention, a transversely extending waist elastic element is positioned between the end marginal portions of the topsheet and the backsheet. In this regard, upper and lower adhesive coatings are provided which respectively secure the waist elastic element to the topsheet and backsheet.

Notably, the upper adhesive coating securing the waist elastic to the topsheet comprises a substantially overall coating of adhesive between the elastic and the nonwoven fabric of the topsheet. The overall adhesive coating may comprise a continuous adhesive layer, or a filament-type adhesive coating distributed substantially throughout the respective expansive surface of the elastic element, wherein the adhesive filaments themselves may cover as little as 10 percent of the surface area of the elastic element. By this arrangement, the waist elastic element elastically gathers the topsheet nonwoven fabric to form a large plurality of relatively small surface irregularities. In part by virtue of the nonwoven fabric from which the topsheet is formed, these surface irregularities provide a textured and cushioned surface at the inside surface of the diaper waistband which contacts the wearer, thus enhancing the overall comfort of the diaper.

It is contemplated that various forms of adhesive coatings can be provided for the upper adhesive material. For example, the substantially overall coating of adhesive at the upper layer may comprise slot-coated adhesive, applied in accordance with known forming techniques, thus forming a substantially continuous adhesive layer. Alternately, the substantially overall upper adhesive coating may be in the form of spray-coated, hot-melt filament adhesives, applied in either a regular or irregular pattern. As will be recognized by those familiar with the art, such spray-coated adhesives effectively overall coat a surface to which they are applied, by virtue of the large number of filaments applied to the surface in adjacent and overlapping relationship. While the filaments of such spray-coated adhesives may cover as little as 10 percent of the surface area to which they are applied, the distribution of the filaments substantially throughout the extent of the surface provides the desired substantially overall adhesive coating.

While it is contemplated that various types of nonwoven fabric materials can be employed for the topsheet, it is presently preferred that the topsheet material comprise a nonwoven fibrous material which is bonded at regularly spaced apart bond points. Materials such as point-bonded, fusible fiber nonwoven fabric, or latex bonded fibrous material bonded in a regular, discontinuous binder pattern, are contemplated. By such an arrangement, the surface irregularities formed at the inside surface of the diaper waistband are provided in a regular pattern which generally corresponds to the regularly spaced apart bond points of the topsheet fabric.

Alternately, the nonwoven topsheet fabric may comprise fibrous material bonded substantially throughout the extent of the fabric, whereby the surface irregularities provided at the inside surface of the waistband are formed in a relatively random fashion. Such topsheet materials typically comprise saturation bonded fabric, or fusible fibrous material subjected to overall heat-calendaring or hot air fusing.

In the preferred form, the elastic element of the present absorbent article comprises heat-shrinkable elastic film material which is suited for adhesive bonding with the associated topsheet and backsheet. Use of this material Permits fabrication of the article while the elastic element is in an elastically stable and extended condition, with the heating of the elastic, after securement in position, shrinking the elastic element and thereafter rendering it elastically extensible and contractible.

Numerous other features and advantages of the present invention will become readily apparent from the following detailed description, the accompanying drawings, and the appended claims.

DETAILED DESCRIPTION

Figure 1:
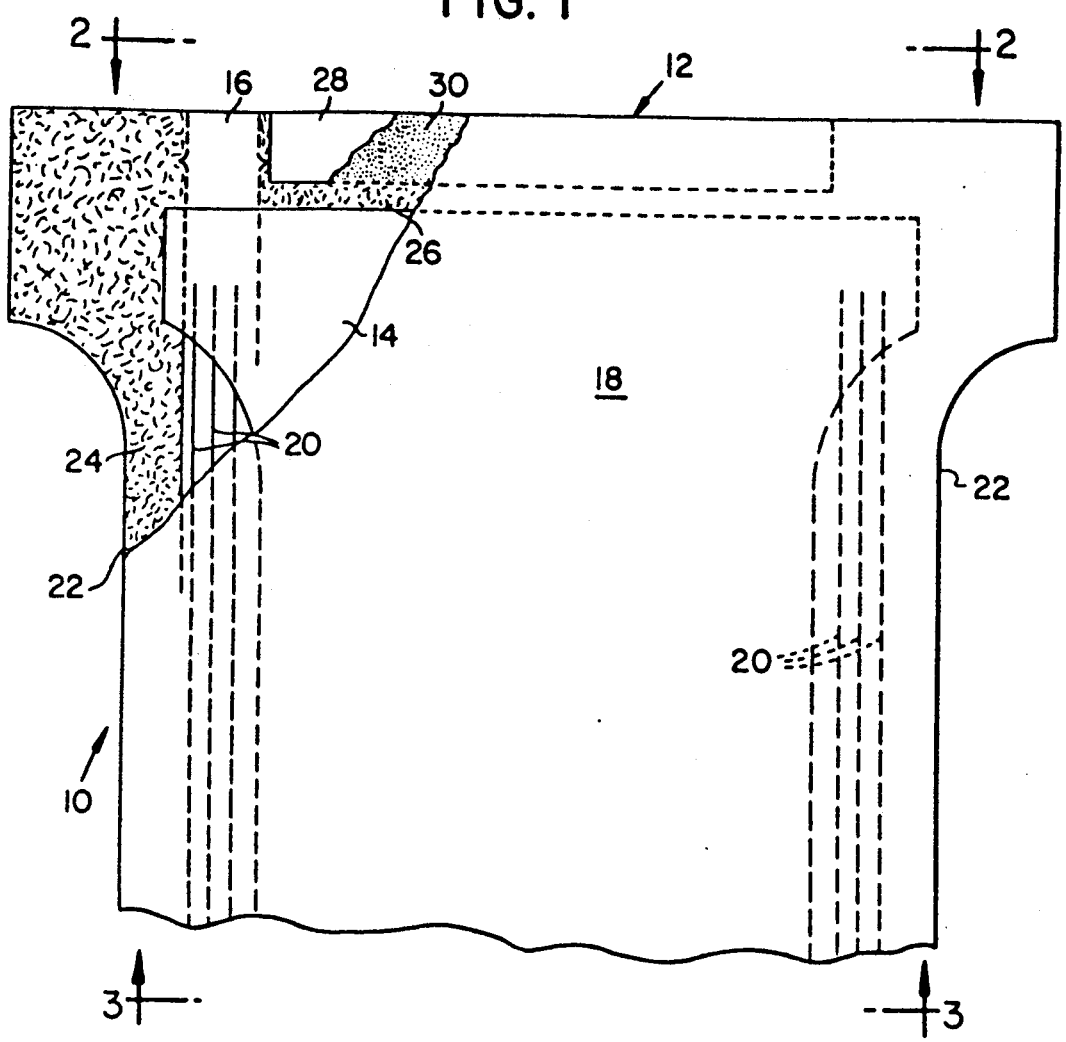
FIG. 1 is a fragmentary, top plan view, partially cut away, of an elasticized disposable absorbent article, illustrated as an elastic waistband disposable diaper, embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

Figure 2:
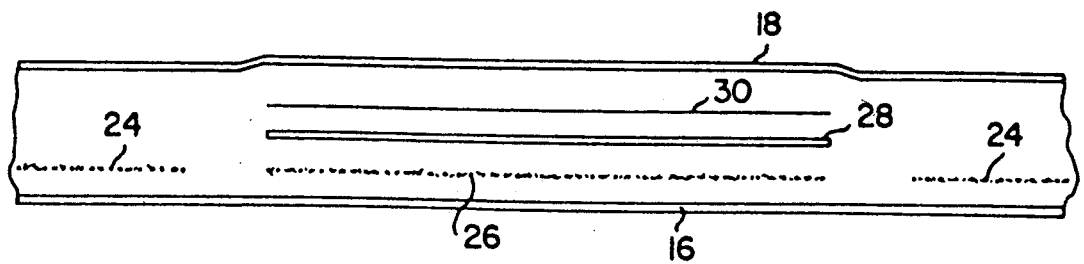
FIG. 2 is an exploded, end view of the diaper shown in FIG. 1 taken generally along lines 2-2 of FIG. 1.
Figure 3:
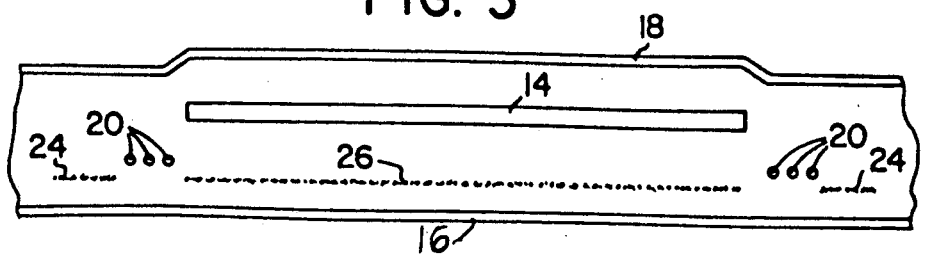
FIG. 3 is an exploded, cross-sectional view of the present disposable diaper taken generally along lines 3—3 of FIG. 1.

With reference first to FIGS. 1-3, therein is illustrated an elasticized absorbent article, illustrated as an elastic waistband disposable diaper 10, having an elastic waistband region 12, embodying the principles of the present invention. The disposable diaper 10 can be readily sized for use by infants and babies of different sizes. The present absorbent article can further readily be configured in relatively larger sizes for incontinence use by adults. Moreover, an elasticized absorbent article embodying the present invention may be configured as any of a variety of other absorbent devices, such as sanitary products.

As illustrated, the disposable diaper 10 includes an absorbent panel 14, which in accordance with known practices, typically comprises comminuted wood pulp fiber ("wood fluff") which is desirably employed because of its highly absorbent nature and its relatively low cost. One or more tissue layers may also be employed in connection with the wood pulp material of absorbent panel 14 for stabilizing and lending integrity to the absorbent panel. In addition, so-called superabsorbent or hydrocolloid materials, typically particulate in nature, may be blended or otherwise combined with the wood pulp material of the absorbent panel 14 for enhancing its absorbent capacity.

In order to provide the desired containment characteristics for the disposable diaper 10, the diaper includes a backsheet 16 positioned beneath the absorbent panel 14, with the backsheet including at least a portion which is liquid impermeable. Such an impermeable portion is at least coextensive with the absorbent panel 14. The backsheet 16 may comprise suitably liquid-impermeable plastic film material, or can be formed from a lamination or other composite construction including a liquid-impermeable barrier layer which is at least coextensive with the absorbent panel 14, joined to a nonwoven and otherwise vapor permeable layer to thereby reduce the overall impermeable surface area of the backsheet 16.

As shown, the backsheet 16 extends beyond the end and side edges of the absorbent panel 14. Specifically, the backsheet includes at least one longitudinal end marginal portion extending beyond the absorbent panel 14 (shown as at its upper edge in the orientation of FIG. 1), and also includes opposite side marginal portions which extend laterally beyond opposite side edges of the absorbent panel 14.

Disposable diaper 10 further includes a liquid-permeable topsheet 18 (sometimes referred to as a facing layer) which overlies the absorbent panel 14, and which comprises nonwoven fabric. The topsheet typically is formed so as to facilitate passage of liquid therethrough and into absorbent panel 14, while the topsheet itself tends to remain dry and resist wicking of liquid toward the edges of the disposable diaper.

Like the backsheet 16, topsheet 18 includes at least one end marginal portion which extends beyond the absorbent panel 14, which end marginal portion is longitudinally coextensive with the end marginal portion of the backsheet at elastic waistband region 12. Moreover, the topsheet 18 includes opposite side marginal portions which extend laterally beyond opposite side edges of the absorbent panel 14.

In accordance with the preferred construction, disposable diaper 10 is provided with an arrangement for effectively gathering the leg-encircling opposite side margins of the diaper. To this end, a plurality of substantially parallel leg elastic elements 20 are positioned between the respective side marginal portions of the topsheet and backsheet at each opposite side of the absorbent panel 14 of the diaper. The leg elastic elements 20 are preferably secured, such as by adhesive coating of the individual elements, to both the topsheet 18 and backsheet 16, with the leg elastics arranged so as to elastically gather and contract the side marginal portions of the topsheet and backsheet in the crotch portion, thereby effectively elasticizing the opposite leg openings 22 of the disposable diaper 10. As will be recognized by those familiar with the art, various forms of leg elastic elements can be employed for achieving the desired elastic gathering of the leg openings 22.

To lend integrity to the diaper structure, the various components of the diaper are preferably secured to each other, such as by adhesive coatings or glue lines, ultrasonic bonding, or the like. In the illustrated embodiment, the backsheet 16 and topsheet 18 are preferably secured to each other, in the side marginal portions thereof generally laterally outwardly of the leg elastic elements 20, by adhesive coating 24. In the illustrated embodiment, adhesive coating 24 comprises spray-coated, hot-melt filament adhesive, which is illustrated as being applied in a relatively random pattern such as is achieved by the use of an Acu-Fiber ™ hot-melt filament applicating system, available from Acumeter Laboratories, Inc., Marlborough, Massachusetts.

As will be recognized by those familiar with the art, this type of applicating system provides a substantially overall coating of hot-melt adhesive in a relatively random filament pattern, with filament diameters on the order of 0.01mm. Other forms of adhesive coating can be employed, such as achieved through the use of a Nordson CF-200 hot-melt spray gun, available from Nordson Corporation, Amherst, Ohio, which system applies a substantially overall adhesive coating in the form of parallel, spiral-like filament patterns. Such spray filament-type adhesives provide a substantially overall coating in the sense that they are distributed substantially throughout the surface to which the spray is applied, even though the filaments themselves may only cover a fraction of the surface area. As is further known in the art, use of parallel, spaced adhesive glue lines can be employed for securing the backsheet and topsheet to each other.

In order to secure the absorbent panel 14 in position, adhesive coating 26 is preferably provided between the absorbent panel and the backsheet 16. Like the adhesive coating 24, adhesive coating 26 may comprise a spray-coated hot-melt filament adhesive.

In accordance with the present invention, the elastic waistband region 12 of disposable diaper 10 includes a transversely extending waist elastic element 28 which is positioned between the end marginal portions of the topsheet 18 and the backsheet 16. Such an elastic element can be provided at either the front or rear waist regions of the diaper, or both, with such waist elastication cooperating with the typical adhesive fastener tape tabs of the diaper (not shown) for conforming the diaper to the wearer.

It is contemplated that the waist elastic element 28 comprise an elastic material which is subject to adhesive bonding, with one particularly preferred material comprising the heat-shrinkable elastic film material which is the subject of commonly-assigned, co-pending U.S. Pat. application Ser. No. 432,834, filed Nov. 7, 1989. However, as will be appreciated, other adhesive-bondable elastic materials may be employed, such as elastic closed cell polyurethane foams, natural and synthetic rubber materials, heat-shrinkable film materials, and like elastic members.

The waist elastic element 28 is preferably secured to the associated topsheet 18 and backsheet 16 by upper and lower adhesive coatings, each of which preferably substantially overall cover and coat the respective opposite sides of the elastic element 28. To this end, the upper adhesive coating 30 may comprise a slot-coated hot-melt adhesive coating which secures the elastic element 28 to the topsheet 18. In contrast, the lower adhesive coating may comprise the adhesive coating 26 between the backsheet 16 and the absorbent panel 14, with the adhesive coating 26 extending to the region between the elastic element 28 and the backsheet 16.

While the upper adhesive layer 30 between the elastic element 28 and the topsheet 18 is illustrated as comprising slot-coated adhesive, it is contemplated that a substantially similar, substantially overall coating of adhesive can alternately be provided by a spray-coated hot-melt filament adhesive coating, such as provided at 24 and 26 (either in the form of a substantially random filament pattern, or in a regular filament pattern, as discussed above). As noted, such spray filament-type adhesives effectively provide a network of adhesive filaments which are distributed substantially throughout the surface to which they are applied.

It should be noted that when the present diaper includes a waist elastic element 28 comprising heat-shrinkable elastic material, the slot-coated or spray hot-melt adhesive should be applied to the associated backsheet and/or topsheet, and not directly to the heat-shrinkable elastic. This avoids activation of the heat-shrinking by application of the adhesive directly on the elastic element.

Figure 5:
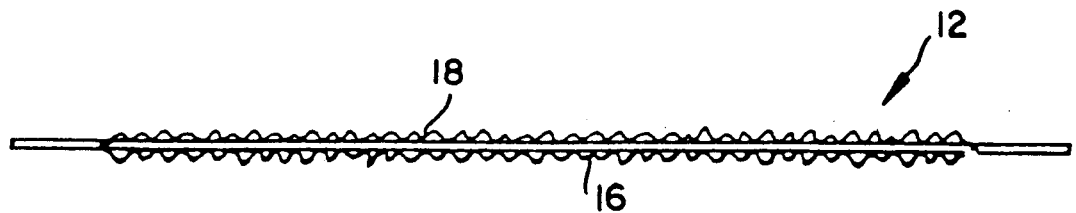
FIG. 5 is an end view of an elastic waistband region of the present disposable diaper.
Figure 4:
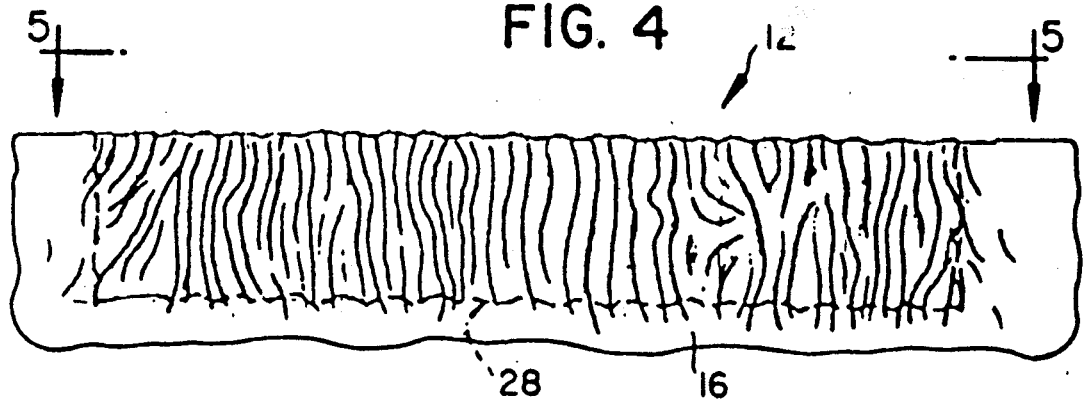
FIG. 4 is a photographic view of the inside surface of the elastic waistband region of FIG. 5.

The significance of the provision of a substantially overall adhesive coating for the upper adhesive between the elastic element 28 and the topsheet 18 is the resultant highly desirable interior texturing of the inside surface of the waistband region 12. Specifically, the overall adhesive coating 30 acts in cooperation with the gathering effect of the waist elastic element 28 and the nonwoven fabric of the topsheet 18 to form a large plurality of relatively small surface irregularities at the inside surface of the waistband. This resultant effect, which is illustrated in FIG. 5, provides a textured and cushioned surface for contact with the wearer of the diaper, thereby providing desirably enhanced comfort.

While this desired texturing and cushioning can be achieved with any of a variety of nonwoven fabric topsheet materials, it is particularly preferred that the nonwoven fabric material of the topsheet 18 comprise nonwoven fibrous material bonded at regularly spaced apart bond points, whereby the surface irregularities formed at the inside surface of the waistband are provided in a regular pattern generally corresponding to the regularly spaced apart bond points of the topsheet. By way of example, such topsheet material may comprise a point-bonded, fusible fiber fabric, or a latex bonded fibrous nonwoven fabric, bonded in a regular, discontinuous binder pattern, as are known in the art.

Alternately, the topsheet material may comprise nonwoven fibrous material bonded substantially throughout the extent of the fabric, wherein the surface irregularities at the inside surface of the waistband region 12 are provided in relatively random fashion. Topsheet materials of this nature may comprise saturation bonded nonwoven fabric, or fabric comprising fusible fibrous material, with the fabric overall heat-bonded, such as by heat-calendaring or by passage of hot air through the fabric, whereby the individual fusible fibers bond to each other at individual bond points where the fibers intersect.

The preferred use of a topsheet nonwoven fabric having regularly spaced apart bond points, in combination with the substantially overall adhesive coating at the upper surface of waist elastic element 28 is believed to enhance the desired texturing and surface irregularities in accordance with the present invention. Specifically, the overall coating of adhesive bonds the waist elastic element 28 to the topsheet fabric such that the fibrous material of the topsheet fabric, between the individual bond points, can bunch-up or puff-up to provide a nub-like texturing effect upon gathering of the topsheet fabric by the elastic element.

Figure 6:
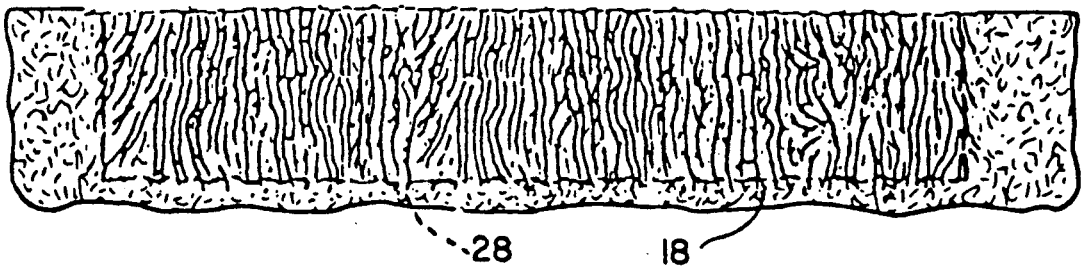
FIG. 6 is a photographic view of an outside surface of the elastic waistband region of the present diaper.

As noted above, the lower adhesive layer, beneath the waist elastic element 28 securing it to backsheet 16, also preferably comprises a substantially overall coating of adhesive. This is preferred since this construction provides a cooperation between the elastic element 28 and the backsheet material whereby an aesthetically-pleasing elastic gathering is achieved, as illustrated in FIG. 6. This arrangement provides a textured, cushioned surface at the outside of the waistband region which also is formed with surface irregularities. This desired effect can be enhanced through the use of a "macro-embossed" film at the diaper backsheet which can be selected to enhance the texturing and cushioning achieved at the outside surface of the waistband.

Another desirable feature of this preferred bonding between the waist elastic element and the backsheet relates to the containment characteristics of the diaper. Specifically, the preferred substantially overall adhesive coating (either slot-coated or spray filament) avoids the formation of any liquid-conducting channels or passages, across the elastic element, from the interior of the diaper to the outside edge of the waistband. This is in significant distinction from prior art constructions, wherein channels which span or traverse the waist elastic element are formed, and which channels undesirably permit end leakage of the diaper. Thus, the present construction exhibits enhanced containment, in addition to improved comfort and aesthetic appeal.

From the foregoing, it will be observed that numerous modifications of the present invention can be achieved without departing from the inventive spirit thereof. It is to be understood that no limitation with respect po the specific embodiment is intended or should be inferred. The disclosure is intended to cover, by the appended claims, all such modifications as fall within the scope of the claims.

What is claimed is:

1. An elasticized disposable absorbent article, comprising:
   an absorbent panel having a first face and a second face;
   a backsheet overlying said second face of said absorbent panel and having at least a portion which is liquid-impermeable, said backsheet having at least one end marginal portion extending beyond said absorbent panel;
   a liquid-impermeable topsheet overlying said first face of said absorbent panel and comprising nonwoven fabric, said topsheet having at least one end marginal portion extending beyond said absorbent panel coextensive with and in face to face relationship with said end marginal portion of said backsheet;
   a waist elastic element comprising a film material rendered elastically extensible and contractable upon heating and positioned between said end marginal portions of said topsheet and said backsheet; and
   upper and lower adhesive means respectively securing said waist elastic element to said topsheet and to said backsheet, said upper adhesive means comprising a substantially overall coating of adhesive between said waist elastic element and said nonwoven fabric of said topsheet, whereby said waist elastic element elastically gathers said topsheet nonwoven fabric to form a large plurality of relatively small surface irregularities providing a textured and cushioned surface for contact with the wearer of said article for enhanced comfort.

2. The elasticized disposable absorbent article in accordance with claim 1 wherein said absorbent article comprises a disposable diaper;
   said absorbent panel comprises at least one end, two opposite sides, and each of said sides has a side edge;
   said coextensive marginal end portions of said backsheet and said topsheet extend longitudinally beyond said at least one end of said absorbent panel, and said waist elastic element extends transversely between said coextensive marginal end portions;
   each of said backsheet and said topsheet includes opposite side marginal portions extending laterally beyond each of said side edges of said absorbent panel; and
   said diaper includes leg elastic means operatively associated with said side marginal portions of said topsheet and said backsheet and said leg elastic means comprises a plurality of substantially parallel leg elastic elements positioned between respective said side marginal portions of said topsheet and said backsheet at each said opposite side of said absorbent panel.

3. The elasticized disposable absorbent article in accordance with claim 1, wherein
   said nonwoven topsheet fabric comprises nonwoven fibrous material bonded substantially throughout the extent of said fabric, whereby said surface irregularities are provided in a relatively random fashion.

4. The elasticized disposable absorbent article in accordance with claim 1, wherein
   said topsheet fabric comprises saturation bonded nonwoven fabric.

5. The elasticized disposable absorbent article in accordance with claim 1, wherein
said topsheet fabric comprises fusible fibrous material, said fabric being overall heat-bonded.

6. The elasticized disposable absorbent article in accordance with claim 1, wherein
said nonwoven topsheet fabric comprises nonwoven fibrous material bonded at regularly spaced apart bond points, whereby said surface irregularities are provided in a regular pattern generally corresponding to said regularly spaced apart bond points.

7. The elasticized disposable absorbent article in accordance with claim 1, wherein
said topsheet fabric comprises point-bonded, fusible fiber fabric.

8. The elasticized disposable absorbent article in accordance with claim 1, wherein
said topsheet fabric comprises latex bonded fibrous material bonded in a regular, discontinuous binder pattern.

9. The elasticized disposable absorbent article in accordance with claim 1 wherein
said adhesive coating of said upper adhesive means comprises a slot-coated adhesive.

10. An elasticized disposable absorbent article, comprising:
an absorbent panel having a first face and a second face;
a backsheet overlying said second face of said absorbent panel and having at least a portion which is liquid-impermeable, said backsheet having at least one end marginal portion extending beyond said absorbent panel;
a liquid-permeable topsheet overlying said first face of said absorbent panel and comprising nonwoven fabric, said topsheet having at least one end marginal portion extending beyond said absorbent panel coextensive with and in face to face relationship with said end marginal portion of said backsheet;
a waist elastic element comprising an elastic closed cell polyurethane foam positioned between said end marginal portions of said topsheet and said backsheet; and
upper and lower adhesive means respectively securing said waist elastic element to said topsheet and to said backsheet, said upper adhesive means comprising a substantially overall coating of adhesive between said waist elastic element and said nonwoven fabric of said topsheet, whereby said waist elastic element elastically gathers said topsheet nonwoven fabric to form a large plurality of relatively small surface irregularities providing a textured and cushioned surface for contact with the wearer of said article for enhanced comfort.

11. The elasticized disposable absorbent article in accordance with claim 10 wherein said absorbent article comprises a disposable diaper;
said absorbent panel comprises at least one end, two opposite sides, and each of said sides has a side edge;
said coextensive marginal end portions of said backsheet and said topsheet extend longitudinally beyond said at least one end of said absorbent panel, and said waist elastic element extends transversely between said coextensive marginal end portions;
each of said backsheet and said topsheet includes opposite side marginal portions extending laterally beyond each of said side edges of said absorbent panel; and
said diaper includes leg elastic means operatively associated with said side marginal portions of said topsheet and said backsheet and said leg elastic means comprises a plurality of substantially parallel leg elastic elements positioned between respective said side marginal portions of said topsheet and said backsheet at each said opposite side of said absorbent panel.

12. The elasticized disposable absorbent article in accordance with claim 10, wherein
said nonwoven topsheet fabric comprises nonwoven fibrous material bonded substantially throughout the extent of said fabric, whereby said surface irregularities are provided in a relatively random fashion.

13. The elasticized disposable absorbent article in accordance with claim 10, wherein
said topsheet fabric comprises saturation bonded nonwoven fabric.

14. The elasticized disposable absorbent article in accordance with claim 10, wherein
said topsheet fabric comprises fusible fibrous material, said fabric being overall heat-bonded.

15. The elasticized disposable absorbent article in accordance with claim 10, wherein
said nonwoven topsheet fabric comprises nonwoven fibrous material bonded at regularly spaced apart bond points, whereby said surface irregularities are provided in a regular pattern generally corresponding to said regularly spaced apart bond points.

16. THe elasticized disposable absorbent article in accordance with claim 10, wherein
said topsheet fabric comprises point-bonded, fusible fiber fabric.

17. The elasticized disposable absorbent article in accordance with claim 10, wherein
said topsheet fabric comprises latex bonded fibrous material bonded in a regular, discontinuous binder pattern.

18. The elasticized disposable absorbent article in accordance with claim 10 wherein
said adhesive coating of said upper adhesive means comprises a slot-coated adhesive.

19. An elasticized disposable absorbent article comprising:
an absorbent panel having a first face and a second face;
a backsheet overlying said second face of said absorbent panel and having at least a portion which is liquid-impermeable, said backsheet having at least one end marginal portion extending beyond said absorbent panel;
a liquid-impermeable topsheet overlying said first face of said absorbent panel and comprising nonwoven fabric, said topsheet having at least one end marginal portion extending beyond said absorbent panel co-extensive with and in face to face relationships with said end marginal portion of said backsheet;
a waist elastic element positioned between said end marginal portions of said topsheet and said backsheet; and
upper and lower adhesive means respectively securing said elastic element to said topsheet and to said backsheet, at least one of said adhesive means comprising a spray-coated, hot-melt filament adhesive and said upper adhesive means comprising a substantially overall coating of adhesive between said waist elastic element and said nonwoven fabric of said topsheet, whereby said waist elastic element elastically gathers said topsheet nonwoven fabric to form a large plurality of relatively small surface irregularities providing a textured and cushioned surface for contact with the wearer of said article for enhanced comfort.

20. The elasticized disposable absorbent article in accordance with claim 19 wherein said absorbent article comprises a disposable diaper;

said absorbent panel comprises at least one end, two opposite sides, and each of said sides has a side edge;

said coextensive marginal end portions of said backsheet and said topsheet extend longitudinally beyond said at least one end of said absorbent panel, and said waist elastic element extends transversely between said coextensive marginal end portions;

each of said backsheet and said topsheet includes opposite side marginal portions extending laterally beyond each of said side edges of said absorbent panel; and said diaper includes leg elastic means operatively associated with said side marginal portions of said topsheet and said backsheet and said leg elastic means comprises a plurality of substantially parallel leg elastic elements positioned between respective said side marginal portions of said topsheet and said backsheet at each said opposite side of said absorbent panel.

21. The elasticized disposable absorbent article in accordance with claim 19, wherein said adhesive coating of said upper adhesive means comprises said spray-coated, hot-melt filament adhesive.

22. The elasticized disposable absorbent article in accordance with claim 19, wherein said lower adhesive means comprises a substantially overall coating of said spray-coated, hot-melt filament adhesive.

23. The elasticized disposable absorbent article in accordance with claim 19, wherein said upper and lower adhesive means comprise said spray-coated, hot-melt filament adhesive.

24. The elasticized disposable absorbent article in accordance with claim 19, wherein said nonwoven topsheet fabric comprises nonwoven fibrous material bonded substantially throughout the extent of said fabric, whereby said surface irregularities are provided in a relatively random fashion.

25. The elasticized disposable absorbent article in accordance with claim 19, wherein said topsheet fabric comprises saturation bonded nonwoven fabric.

26. The elasticized disposable absorbent article in accordance with claim 19, wherein said topsheet fabric comprises fusible fibrous material, said fabric being overall heat-bonded.

27. The elasticized disposable absorbent article in accordance with claim 19, wherein said nonwoven topsheet fabric comprises nonwoven fibrous material bonded at regularly spaced apart bond points, whereby said surface irregularities are provided in a regular pattern generally corresponding to said regularly spaced apart bond points.

28. The elasticized disposable absorbent article in accordance with claim 19, wherein said topsheet fabric comprises point-bonded, fusible fiber fabric.

29. The elasticized disposable absorbent article in accordance with claim 19 wherein said topsheet fabric comprises latex bonded fibrous material bonded in a regular, discontinuous binder pattern.

* * * * *